United States Patent
Tai

(10) Patent No.: US 9,295,422 B2
(45) Date of Patent: Mar. 29, 2016

(54) MULTIFUNCTION FITNESS TESTING DEVICE

(71) Applicant: Hsu-Chih Tai, Tainan (TW)

(72) Inventor: Hsu-Chih Tai, Tainan (TW)

(*) Notice: Subject to any disclaimer, the term of this patent is extended or adjusted under 35 U.S.C. 154(b) by 0 days.

(21) Appl. No.: 14/535,371

(22) Filed: Nov. 7, 2014

(65) Prior Publication Data

US 2015/0128695 A1  May 14, 2015

(30) Foreign Application Priority Data

Nov. 12, 2013 (TW) .............................. 102141078 A

(51) Int. Cl.
- *A61B 5/22* (2006.01)
- *A61B 5/0205* (2006.01)
- *A61B 5/107* (2006.01)
- *A61B 5/00* (2006.01)

(Continued)

(52) U.S. Cl.
CPC ................. *A61B 5/222* (2013.01); *A61B 5/002* (2013.01); *A61B 5/0205* (2013.01); *A61B 5/1072* (2013.01); *A61B 5/224* (2013.01); *A61B 5/4872* (2013.01); *A61B 5/681* (2013.01); *A61B 5/6824* (2013.01); *A61B 5/6826* (2013.01); *A61B 5/6838* (2013.01); *A61B 5/742* (2013.01); *A61B 5/7475* (2013.01); *A63B 21/0442* (2013.01); *A63B 21/0552* (2013.01); *A63B 21/156* (2013.01); *A63B 21/4015* (2015.10); *A63B 21/4029* (2015.10); *A63B 21/4035* (2015.10); *A63B 21/4043* (2015.10); *A63B 22/0694* (2013.01); *A63B 23/0211* (2013.01); *A63B 24/0062* (2013.01); *A63B 24/0087* (2013.01); *G01G 19/50* (2013.01); *A61B 5/024* (2013.01); *A63B 2022/0641* (2013.01); *A63B 2024/0065* (2013.01); *A63B 2024/0068* (2013.01); *A63B 2024/0071* (2013.01); *A63B 2024/0093* (2013.01); *A63B 2071/065* (2013.01); *A63B 2071/0625* (2013.01); *A63B 2220/20* (2013.01); *A63B 2220/30* (2013.01); *A63B 2225/10* (2013.01); *A63B 2225/50* (2013.01); *A63B 2225/54* (2013.01); *A63B 2225/70* (2013.01); *A63B 2230/01* (2013.01); *A63B 2230/70* (2013.01)

(58) Field of Classification Search
CPC ............ A61B 5/22; A61B 1/24; A63B 21/02; G01L 5/00
USPC ......................................... 73/379.01–379.05
See application file for complete search history.

(56) References Cited

U.S. PATENT DOCUMENTS

| | | | |
|---|---|---|---|
| 7,207,932 | B1 | 4/2007 | Dean |
| 7,628,730 | B1 | 12/2009 | Watterson et al. |

(Continued)

FOREIGN PATENT DOCUMENTS

| | | |
|---|---|---|
| TW | I330535 B | 9/2010 |
| TW | I400063 B | 7/2013 |

*Primary Examiner* — Jewel V Thompson

(74) *Attorney, Agent, or Firm* — Alan D. Kamrath; Kamrath IP Lawfirm, P.A.

(57) ABSTRACT

A multifunction fitness testing device is disclosed. The multifunction fitness testing device includes a main body, a muscular endurance test part, a flexibility test part, a grip test part, and a host computer. The muscular endurance test part connects to the main body. The muscular endurance test part includes a foot fixing part and a folding plate. The foot fixing part connects to the folding plate. The flexibility test part is located near the foot fixing part. The host computer connects to the main body and electrically connects to the folding plate, the flexibility test part, and the grip test part.

14 Claims, 14 Drawing Sheets

(51) Int. Cl.
*G01G 19/50* (2006.01)
*A63B 21/04* (2006.01)
*A63B 21/055* (2006.01)
*A63B 21/00* (2006.01)
*A63B 22/06* (2006.01)
*A63B 23/02* (2006.01)
*A63B 24/00* (2006.01)
*A61B 5/024* (2006.01)
*A63B 71/06* (2006.01)

(56) References Cited

U.S. PATENT DOCUMENTS

| | | | | |
|---|---|---|---|---|
| 7,810,392 | B2 * | 10/2010 | Kitagawa | A63B 17/00 73/379.01 |
| 8,105,207 | B1 * | 1/2012 | Lannon | A63B 23/03566 482/1 |
| 2009/0312672 | A1 | 12/2009 | Strang | |

* cited by examiner

MULTIFUNCTION FITNESS TESTING DEVICE

BACKGROUND OF THE INVENTION

1. Field of the Invention

The present invention relates to a multifunction fitness testing device; more particularly, the present invention relates to a multifunction fitness testing device for testing and recording many kinds of fitness information.

2. Description of the Related Art

To efficiently exercise and record a health condition, sports device manufacturers develop many kinds of electronic sport devices, such as the bicycle machine, the treadmill, and the rowing machine. The abovementioned sport devices are used for allowing the user to exercise and recording the fitness data, such the time spent exercising and calories burned by the user.

However, the sport device of the prior art can record only the fitness information related to its own type of sport; for example, the treadmill records only information related to jogging, and the rowing machine records only information related to calories burned by the muscles involved in rowing. If the user wants to do another kind of exercise and record the information on another kind of exercise, the user must buy another sport device lo meet the requirement; however, such a purchase will incur additional costs. Besides, the sport device of the prior art usually occupies a certain amount of space; therefore, for the user, purchasing additional sport devices will entail the use of more living space.

Therefore, there is a need to provide a new fitness device that allows the user to do many kinds of exercise and record information on exercise and fitness.

SUMMARY OF THE INVENTION

It is an object of the present invention to provide a multifunction fitness testing device which has the features of testing and recording many kinds of fitness information.

To achieve the abovementioned object, the multifunction fitness testing device of the present invention includes a main body, a muscular endurance test part, a flexibility test part, a grip test part, and a host computer. The muscular endurance test part is connected to the main body. The muscular endurance test part includes a folding plate and a foot fixing part. The foot fixing part is connected to the folding plate. The flexibility test part is located next to the foot fixing part. The host computer is connected to the main body and electrically connected to the folding plate, the flexibility test part and the grip test part.

According to one embodiment of the present invention, the multifunction fitness testing device further includes a wireless sensor. The wireless sensor is electrically connected to the host computer.

According to one embodiment of the present invention, the multifunction fitness testing device further includes a cardiopulmonary function test part. The cardiopulmonary function test part is electrically connected to the host computer.

According to one embodiment of the present invention, the multifunction fitness testing device further includes a strength test part. The strength test part is electrically connected to the host computer.

According to one embodiment of the present invention, the multifunction fitness testing device further includes a standing long jump test part. The standing long jump test part is electrically connected to the host computer.

According to one embodiment of the present invention, the multifunction fitness testing device further includes a weight and body fat measurement part. The weight and body fat measurement part is electrically connected to the host computer.

According to one embodiment of the present invention, the multifunction fitness testing device further includes a height measurement part. The height measurement part is electrically connected to the host computer.

According to one embodiment of the present invention, the multifunction fitness testing device further includes a finger pulse clamp. The finger pulse clamp is electrically connected to the host computer.

According to one embodiment of the present invention, the multifunction fitness testing device further includes a fingertip clamp. The fingertip clamp is electrically connected to the host computer.

According to one embodiment of the present invention, the multifunction fitness testing device further includes a wrist clamp. The wrist clamp is electrically connected to the host computer.

According to one embodiment of the present invention, the multifunction fitness testing device further includes an arm clamp. The arm clamp is electrically connected to the host computer.

According to one embodiment of the present invention, the host computer further includes a display interface, an input interface, an identification interface, a controller, and a wireless module. The controller is electrically connected to the display interface, the input interface, the identification interface, and the wireless module.

According to one embodiment of the present invention, the host computer further includes a network module. The network module is electrically connected to the controller and a server.

According to one embodiment of the present invention, the finger pulse clamp, the fingertip clamp, the wrist clamp, the arm clamp, the height measurement part, the wireless sensor, the cardiopulmonary function test part, the strength test part, the muscular endurance test part, the standing long jump test part, and the weight and body fat measurement part are electrically connected to the host computer via the radio frequency method.

DETAILED DESCRIPTION OF THE PREFERRED EMBODIMENT

These and other objects and advantages of the present invention will become apparent from the following description of the accompanying drawings, which disclose several embodiments of the present invention. It is to be understood that the drawings are to be used for purposes of illustration only, and not as a definition of the invention.

Figure 1:
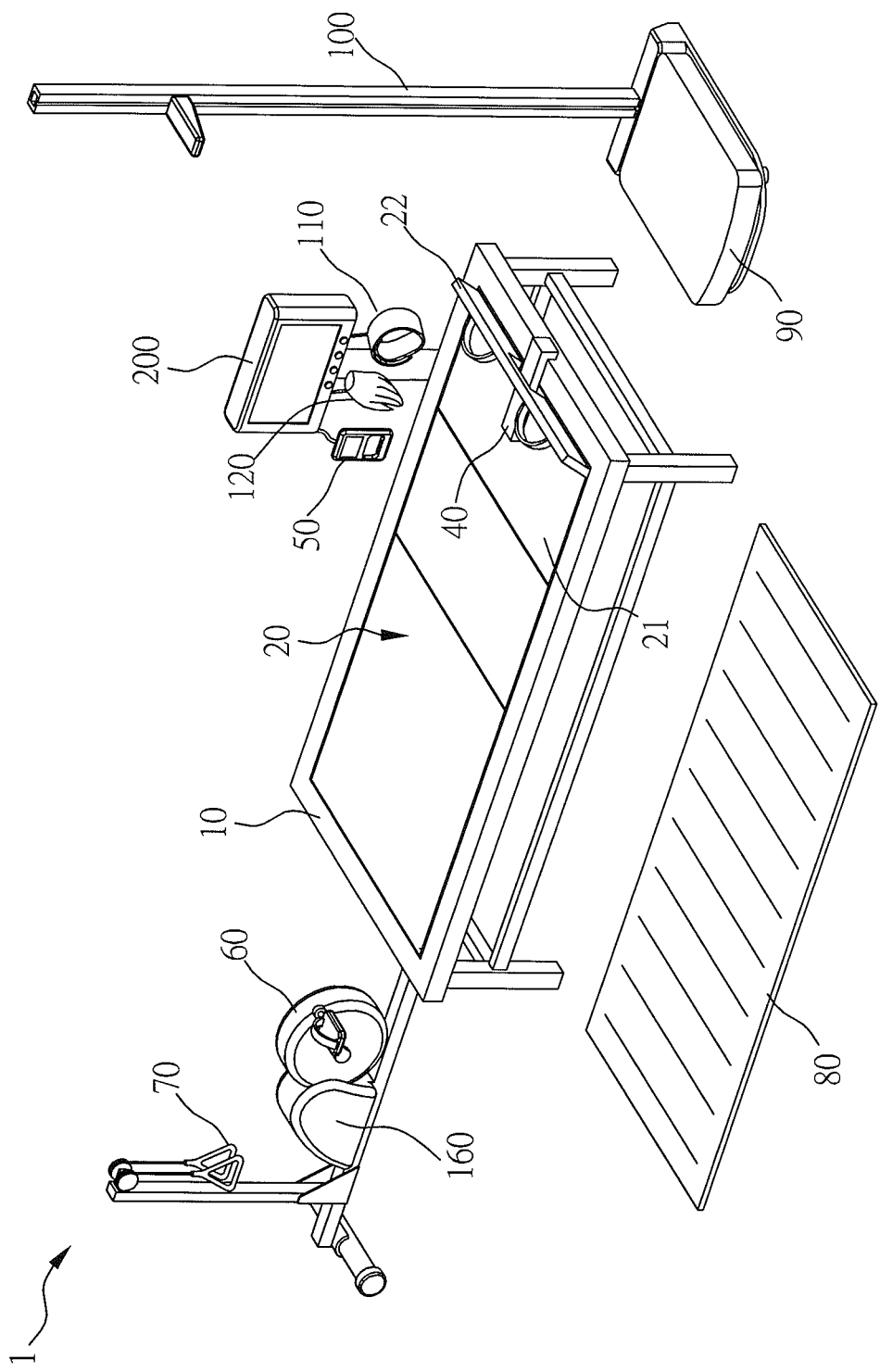
FIG. 1 illustrates a schematic drawing of the multifunction fitness testing device of the first embodiment of the present invention.
Figure 2:
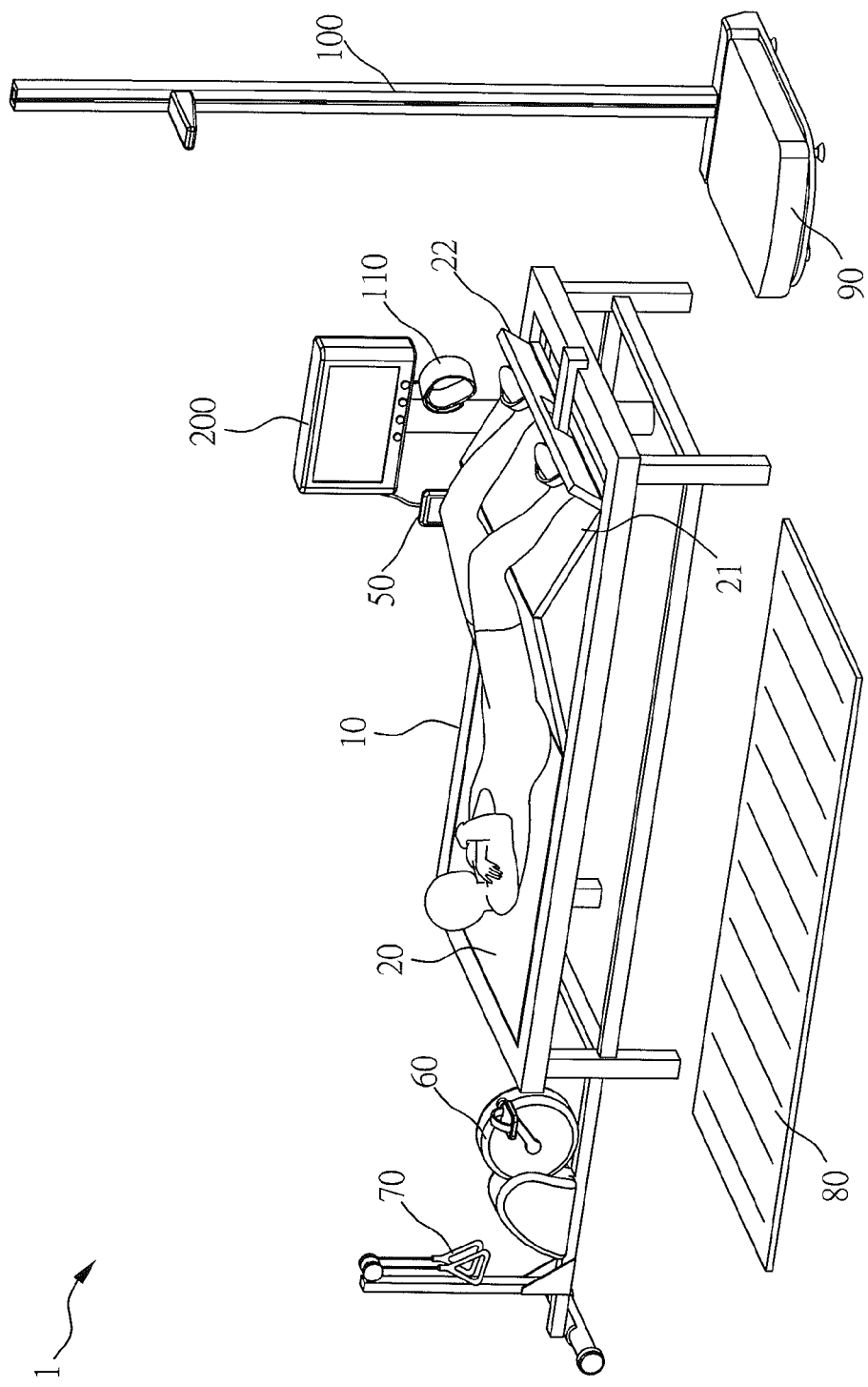
FIG. 2 illustrates a schematic drawing of the muscular endurance test part of the multifunction fitness testing device of the first embodiment of the present invention.
Figure 3:
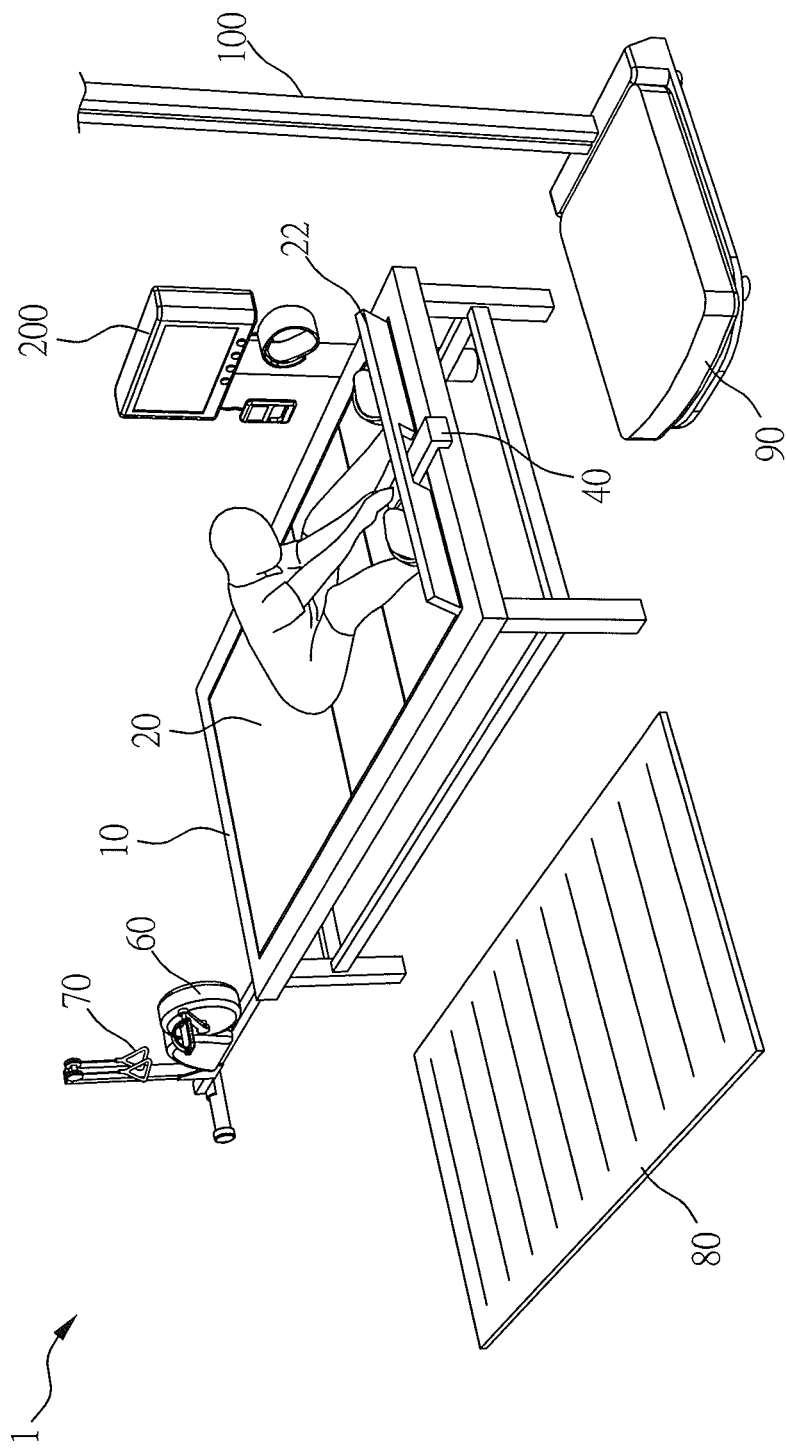
FIG. 3 illustrates a schematic drawing of the flexibility test part of the multifunction fitness testing device of the first embodiment of the present invention.
Figure 4:
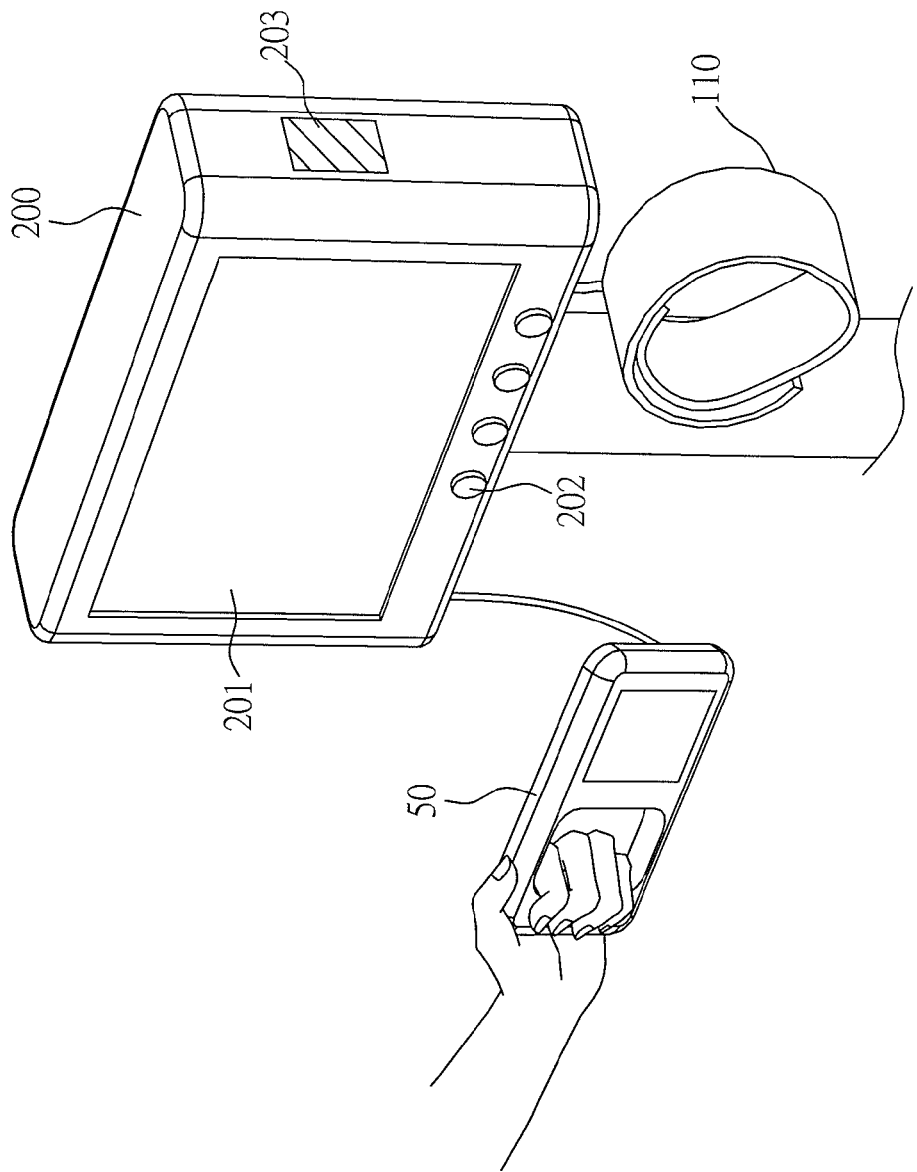
FIG. 4 illustrates a schematic drawing of the grip test part of the multifunction fitness testing device of the first embodiment of the present invention.
Figure 5:
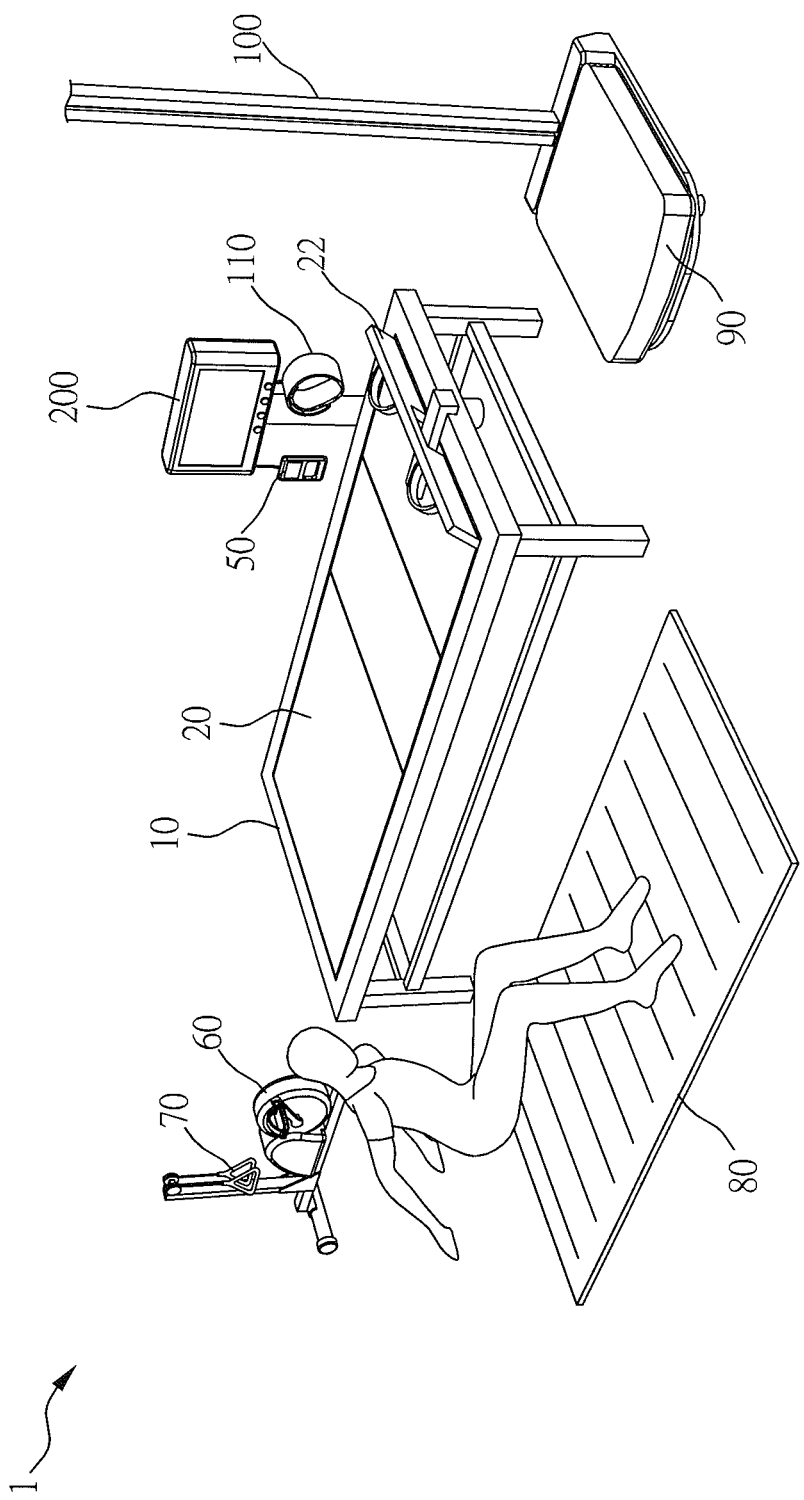
FIG. 5 illustrates a schematic drawing of the standing long jump test part of the multifunction fitness testing device of the first embodiment of the present invention.
Figure 6:
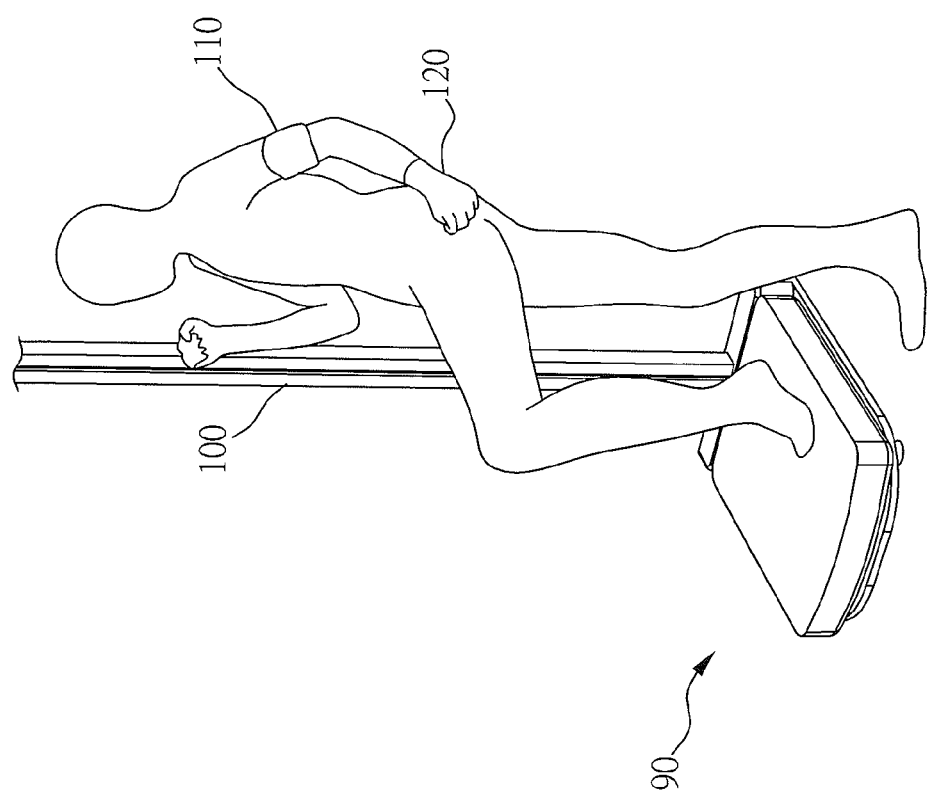
FIG. 6 illustrates a schematic drawing of the weight and body fat measurement part of the multifunction fitness testing device of the first embodiment of the present invention.
Figure 7:
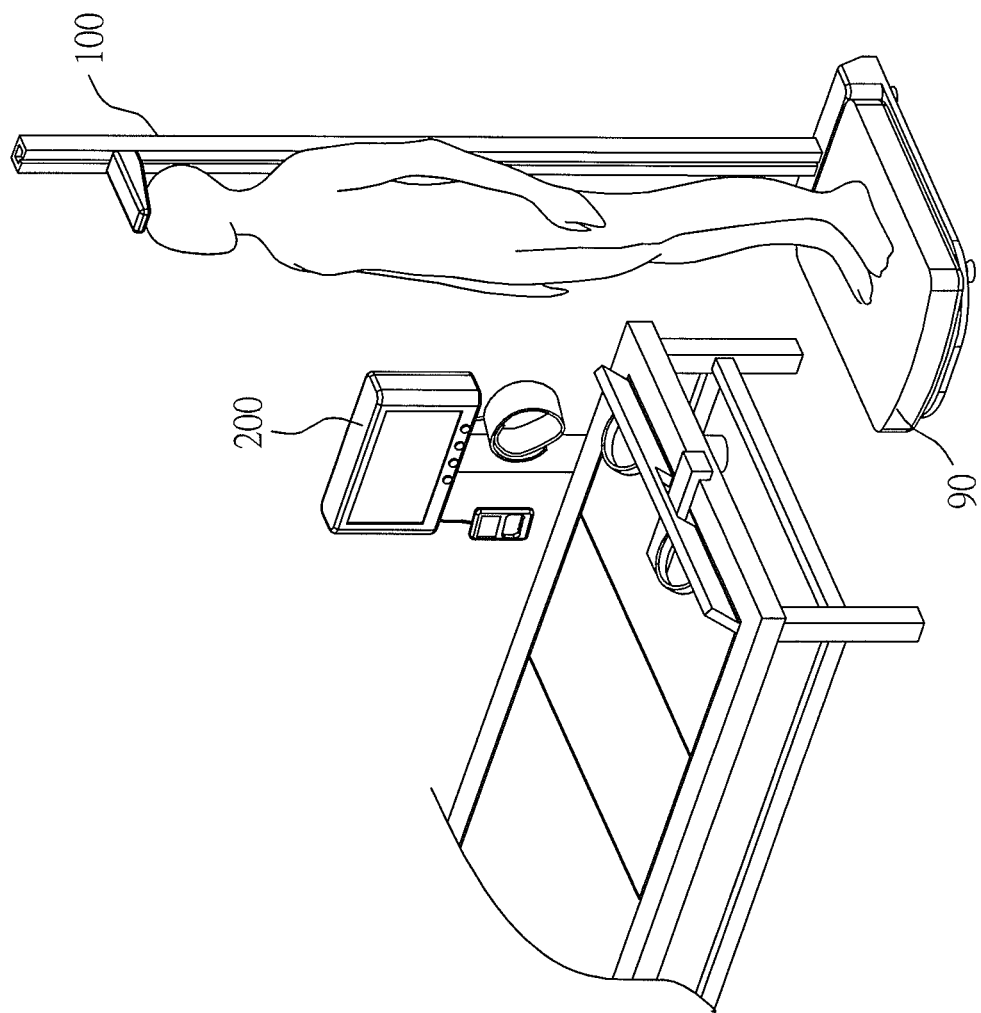
FIG. 7 illustrates a schematic drawing of the height measurement part of the multifunction fitness testing device of the first embodiment of the present invention.
Figure 8:
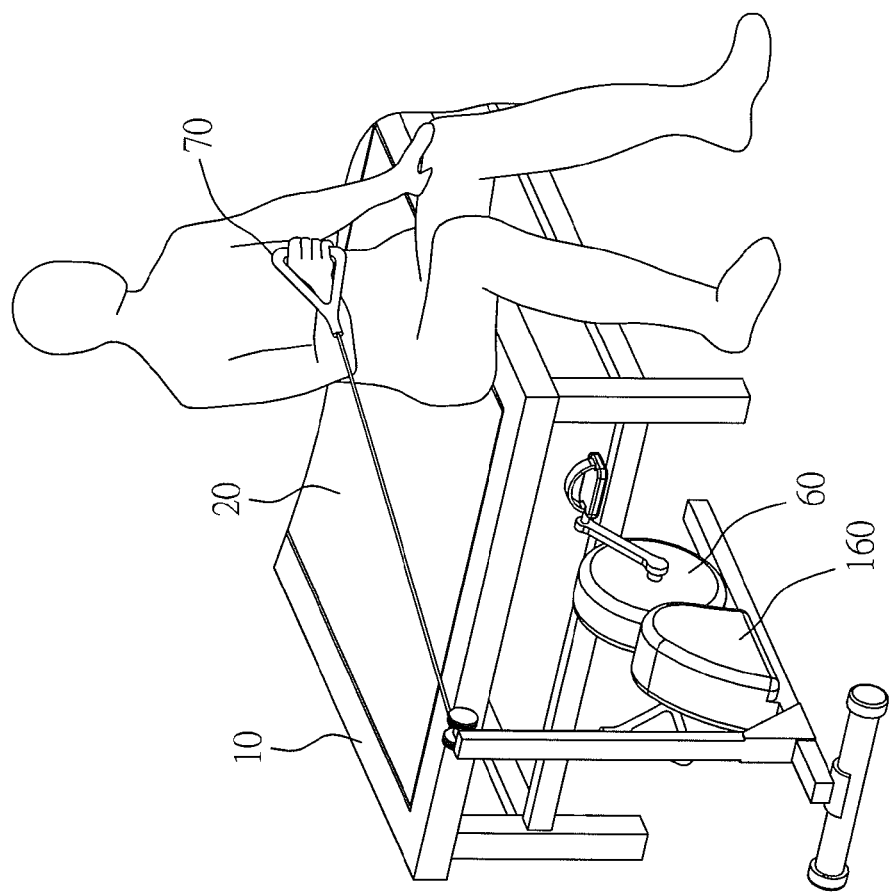
FIG. 8 illustrates a schematic drawing of the strength test part of the multifunction fitness testing device of the first embodiment of the present invention.
Figure 9:
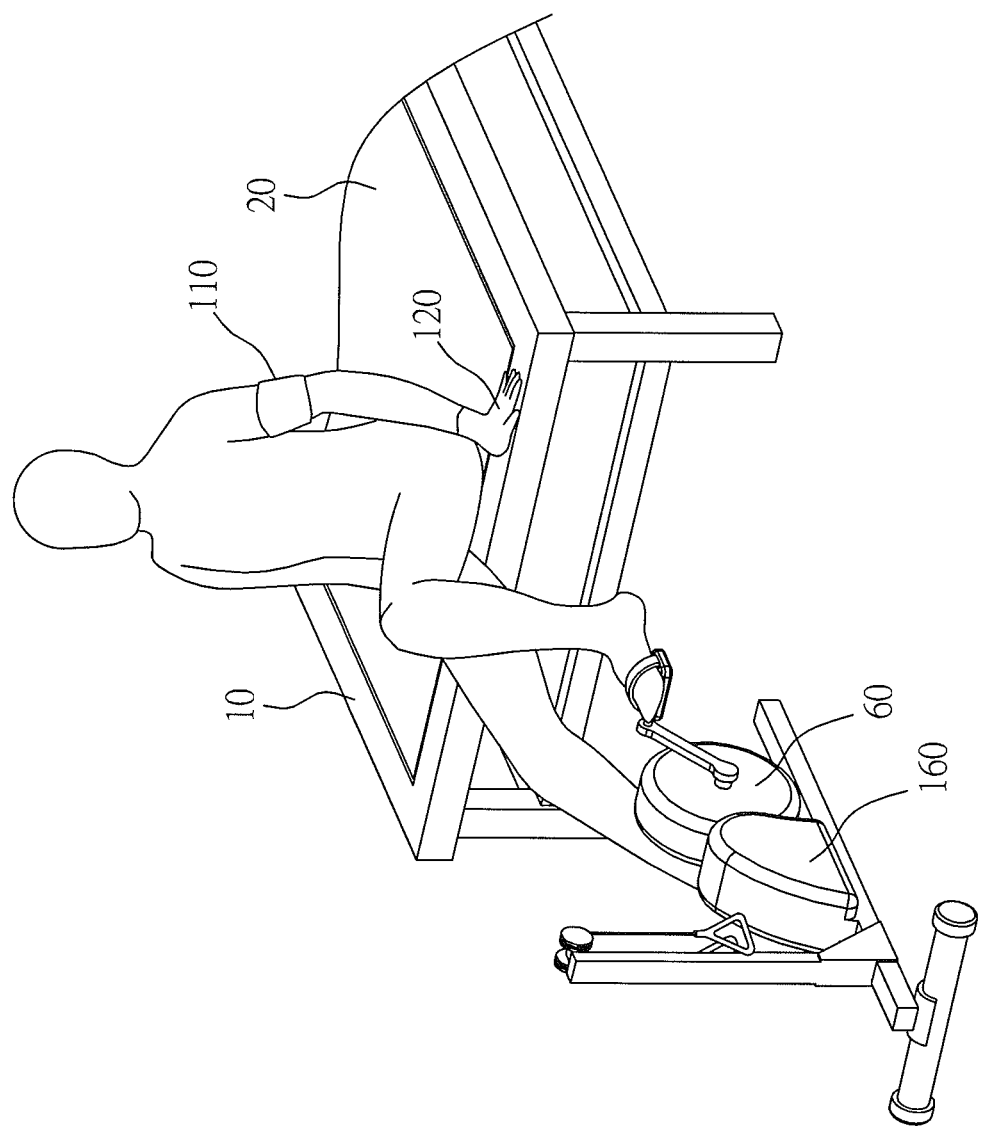
FIG. 9 illustrates a schematic drawing of the cardiopulmonary function test part of the multifunction fitness testing device of the first embodiment of the present invention.
Figure 10:
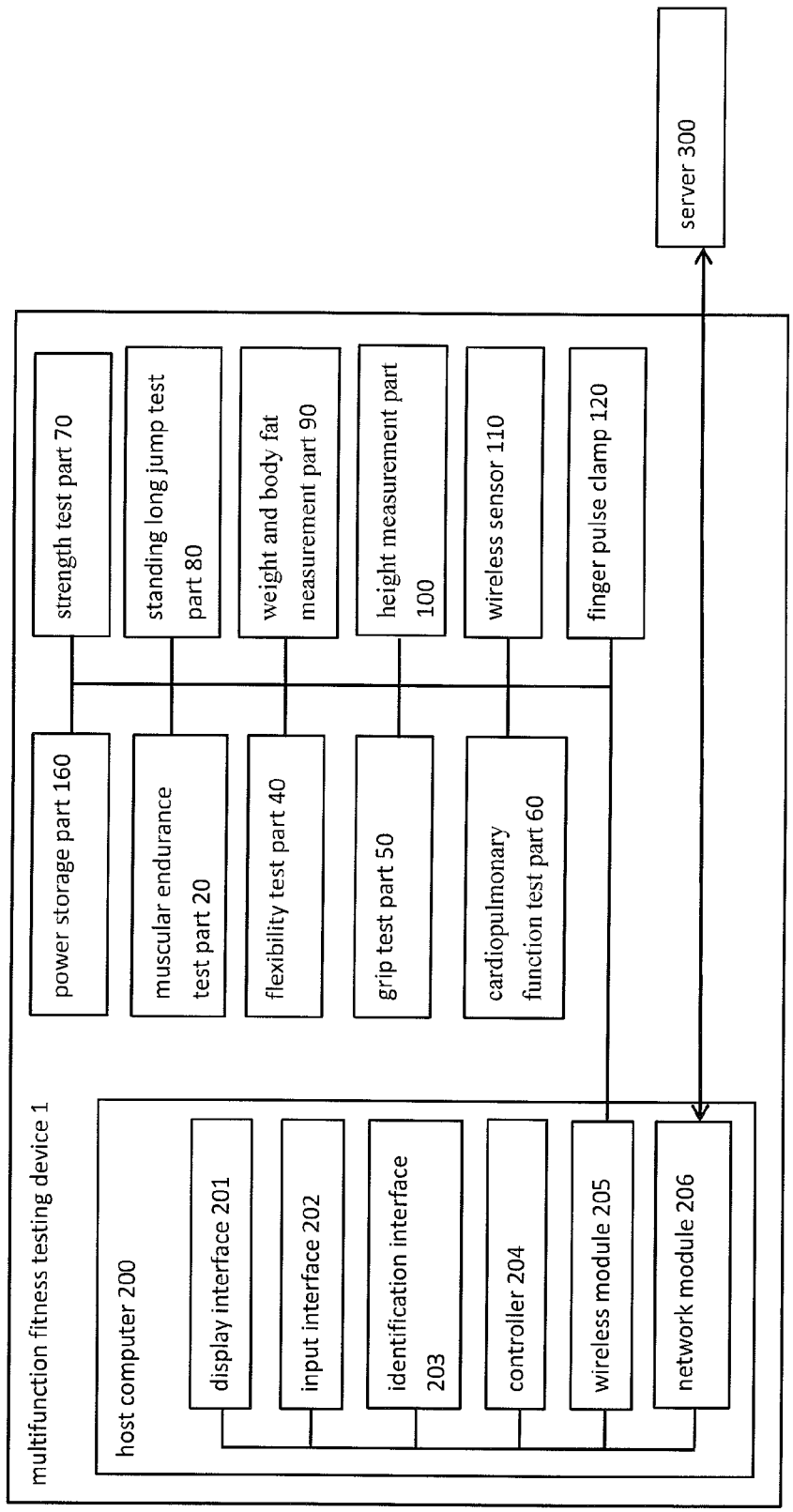
FIG. 10 illustrates a system structure drawing of the multifunction fitness testing device of the first embodiment of the present invention.

Please refer to FIG. 1 to FIG. 10 regarding the multifunction fitness testing device of the first embodiment of the present invention. FIG. 1 illustrates a schematic drawing of the multifunction fitness testing device of the first embodiment of the present invention. FIG. 2 illustrates a schematic drawing of the muscular endurance test part of the multifunction fitness testing device of the first embodiment of the present invention. FIG. 3 illustrates a schematic drawing of the flexibility test part of the multifunction fitness testing device of the first embodiment of the present invention. FIG. 4 illustrates a schematic drawing of the grip test part of the multifunction fitness testing device of the first embodiment of the present invention. FIG. 5 illustrates a schematic drawing of the standing long jump test part of the multifunction fitness testing device of the first embodiment of the present invention. FIG. 6 illustrates a schematic drawing of the weight and body fat measurement part of the multifunction fitness testing device of the first embodiment of the present invention. FIG. 7 illustrates a schematic drawing of the height measurement part of the multifunction fitness testing device of the first embodiment of the present invention. FIG. 8 illustrates a schematic drawing of the strength test part of the multifunction fitness testing device of the first embodiment of the present invention. FIG. 9 illustrates a schematic drawing of the cardiopulmonary function test part of the multifunction fitness testing device of the first embodiment of the present invention. FIG. 10 illustrates a system structure drawing of the multifunction fitness testing device of the first embodiment of the present invention.

As shown in FIG. 1, FIG. 4, FIG. 6 and FIG. 10, in the first embodiment of the present invention, the multifunction fitness testing device 1 includes a main body 10, a muscular endurance test part 20, a flexibility test part 40, a grip test part 50, a cardiopulmonary function test part 60, a strength test part 70, a standing long jump test part 80, a weight and body fat measurement part 90, a height measurement part 100, a host computer 200, a wireless sensor 110, a finger pulse clamp 120, and a power storage part 160. The wireless sensor 110 of the present invention is a removable armband for obtaining vital information (such as the heartbeat or the body temperature) of the user. The wireless sensor 110 is provided for the user to wear on the arm and to sense the body state of the user while exercising. The finger pulse clamp 120 is designed as a glove provided for the user to wear on the hand; the finger pulse clamp 120 is used for sensing the pulse of the user via infrared light and sensing the oxygen and the blood pressure of the user.

The host computer 200 of the present invention is used for recording the fitness information or the identify information of the user when using the multifunction fitness testing device 1 and for transferring the information to a cloud server 300. The host computer 200 includes a display interface 201, an input interface 202, an identification interface 203, a controller 204, a wireless module 205, and a network module 206. The controller 204 is electrically connected to the display interface 201, the input interface 202, the identification interface 203, the wireless module 205, and the network module 206. The controller 204 is a central processing unit (CPU) processor used for controlling the functions of the internal components of the host computer 200. An operating system (such as Windows, OS X, Android, or Linux) and domestic fitness norm values can be installed into the host computer 200, such that the system of the host computer 200 can automatically detect and determine the sport performance of the user, and the system can automatically compare the sport performance to the norm values and determine the performance according to the personal detecting information. The host computer 200 is rotatably connected to the main body 10. The user can adjust the rotation angle of the host computer 200 to view the display interface 201 of the host computer 200 from different positions.

The display interface 201 is used for displaying the information for the user to view and for playing notification sounds to notify the user about the operation processes of the multifunction fitness testing device 1, or for providing teaching or guiding information, allowing the user to understand the multiple functions of the multifunction fitness testing device 1. The input interface 202 is used for inputting fitness information, such as the height, the weight, the waist circumference, the hip circumference, the blood pressure, the glucose, the glycated hemoglobin, the cholesterol, or the uric acid of the user, or for inputting identify information, such as an identifying code, an identification card number, a name, a gender, a profession, a birthday, an E-Mail address, or a home address; however, the inputted information is not limited to the above-mentioned description; in addition, the method of inputting information is not limited to the input interface 202; for example, the host computer 200 may include a cellphone number database and a cellphone inputting software such that the user can use the cellphone to dial a specific number to communicate with the host computer 200 and use the number or text input method of the cellphone to input the information.

The identification interface 203 can be a radio frequency identification (RFID) card, a radio frequency (RF) card, or an RF-SIM card read-write module and is for allowing the user to be identified; therefore, the user can apply a chip card, a health insurance card, a metro card, a student card, a cellphone, or other device with sensing feature to the identification interface 203, such that the identification interface 203 can sense the device of the user to identity the user. However, the identification method of the present invention is not limited to using the identification interface 203; the user can also use the input interface 202 to input corresponding information (an identification card number, a cellphone number, an E-mail address, a code, etc.) as identification information. Via the identity checking method of the identification interface 203, different user permissions can be assigned to users of different identities for managing the data recorded in the host computer 200 of the present invention.

The wireless module 205 is electrically connected to the muscular endurance test part 20, the flexibility test part 40, the grip test part 50, the cardiopulmonary function test part 60, the strength test part 70, the standing long jump test part 80, the weight and body fat measurement part 90, the height measurement part 100 and the wireless sensor 110 via a wireless method such that the sport information of the user can be transferred to the host computer 200 via the wireless module 205 when using the abovementioned elements to exercise. The wireless connecting method of the wireless module 205 of the present invention is a radio frequency, but the wireless connecting method of the present invention is not limited to that design.

The network module 206 is used for communicating to the cloud server 300 to transfer the fitness information, the identity information, or the sport information to the server 300. Therefore, the server 300 can serve as a platform for an application system, such as a health food cloud application system, a market cloud application system, a sport cloud application system, a leisure and tourism cloud application system, or a health care assessment and exercise recommendation application system, to combine the fitness information, the identity information, or the sport information in the application systems such that the user can manage food, fitness and the living conditions via the application system and the server 300 so as to maintain the health of the user. The server 300 can also arrange and manage the fitness information, the identity information, or the sport information of the user, such as analyzing and ranking the fitness information for different years, ages or areas, and provide the results of the analysis to the user, a friend, or the health consultant team via a cellphone messaging or E-mail service to execute related health checks and health care; therefore, the user can completely grasp his or her own exercise condition (for example, the server 300 can provide the user fitness comparison results, before-and-after sport comparison results, before-and-after health care comparison results, the food control comparison results, a specify type of comparison results, and other multifunctional cross-comparisons of the average values of the same ages and the user). After the user receives the integrated results sent from the server 300, the user can choose to print the information or share the information on a community website (such as Facebook or Twitter) to share the sport performance or the health condition information with friends, family, or a specific group.

The host computer 200 also has a storage device and a database for storing and managing the abovementioned fitness information, the identity information, or the sport information generated when the user operates the multifunction fitness testing device 1; however, using the storage device to store the information is not the main object of the present invention, and this feature is already disclosed in the related field of information storing computer devices; therefore, there is no need for further description in the present invention.

As shown in FIG. 2 and FIG. 10, in the first embodiment of the present invention, the muscular endurance test part 20 is connected to the main body 10. The muscular endurance test part 20 includes a folding plate 21 and a foot fixing part 22. The foot fixing part 22 is connected to the folding plate 21.

The folding plate 21 is used for the user to sit down or lie down, and the folding plate 21 can be folded according to the body angle of the user. The surface of folding plate 21 is made of a waterproof material to prevent the sweat of the user attaching to the folding plate 21, and the user can easily wash and clean the folding plate 21 with water. The foot fixing part 22 is used for temporarily and partially restraining the user such that the user can exercise. For example, the user can lie down on the folding plate 21, fasten the feet on the foot fixing part 22, and bend the folding plate 21 to meet the angle of the feet of the user, whereby the user can do sit-ups. A pressure sensing device can be installed in the folding plate 21 of the present invention for sensing the pressure changes of the user when the user is doing sit-ups and for recording the exercise information on the sit-ups (such as the exercise rate, the exercise time, and the number of repetitions), and the folding plate 21 can send the exercise information on sit-ups to the wireless module 205 so that the host computer 200 can manage the exercise information on sit-ups of the user and display the exercise information to the user. However, the sensing method and application method of the muscular endurance test part 20 are not limited to the abovementioned description; for example, an infrared light sensor can be installed in the muscular endurance test part 20 for sensing the height changes of the user from lying down to sitting up during the sit-ups exercise for analyzing the exercise information on sit-ups; the user can also use the pressure sensing device of the muscular endurance test part 20 or the abovementioned infrared light sensor to measure the user's height and the weight; in addition, pressure sensing devices can also be installed on the four supporting columns of the main body 10 of the present invention such that when the user lies down on the muscular endurance test part 20, the pressure sensing devices on the four supporting columns of the main body 10 can measure the weight of the user.

As shown in FIG. 3 and FIG. 10, in the first embodiment of the present invention, the flexibility test part 40 is located next to the foot fixing part 22 for measuring the flexibility of the body of the user. The flexibility test part 40 has a sensing pushing plate used for allowing the user to push for a certain distance such that the flexibility of the body of the user can be measured according to the pushing distance. However, in the field of measuring flexibility, the design of the sensing pushing plate is already disclosed; therefore, there is no need for further description for the design of the sensing pushing plate of the present invention. When actually using the flexibility test part 40 of the present invention, the user can also sit on the muscular endurance test part 20, fasten the feet on the foot fixing part 22, and use at least one hand to touch the flexibility test part 40. The flexibility test part 40 can obtain the flexibility of the body of the user via measuring the distance of the sensing pushing plate pushed by the user's at least one hand and transfer the exercise information on body flexibility to the wireless module 205 so that the host computer 200 can manage the exercise information on the body flexibility of the user and display the information for the user.

As shown in FIG. 4 and FIG. 10, in the first embodiment of the present invention, the grip test part 50 is an ergonomic hand grip ring for measuring the grip strength of the user. The grip test part 50 can transfer the exercise information on grip to the wireless module 205 so that the host computer 200 can manage the exercise information on the grip strength of the user and display the information for the user. The grip test part 50 can be set to measure the grip for 1~3 times, after which the host computer 200 calculates the average grip strength value or captures the best grip strength value to serve as the final grip information.

As shown in FIG. 5 and FIG. 10, in the first embodiment of the present invention, the standing long jump test part 80 is a plate with a distance scale provided for the user to standing long jump and measure the jumping distance. A pressure sensor can be also installed in the standing long jump test part 80; after the user long jumps, the pressure sensor will detect the position of being under pressure to obtain the jumping distance of the user. The standing long jump test part 80 can transfer the exercise information on the standing long jump to the wireless module 205 so that the host computer 200 can manage the exercise information on the standing long jump of the user and display the information for the user. When the user does not need to use the standing long jump test part 80, the user can put the standing long jump test part 80 into the space under the main body 10 to reduce the space occupied by the multifunction fitness testing device 1.

As shown in FIG. 6, FIG. 7 and FIG. 10, in the first embodiment of the present invention, the weight and body fat measurement part 90 is a platform with the features of weight sensing, body fat calculation, and broadcasting. The height measurement part 100 is a stand for measuring the height of the user. The user can use the weight and body fat measurement part 90 to measure the weight and body fat, and use the height measurement part 100 to measure the height. The weight and body fat measurement part 90 and the height measurement part 100 can transfer the height, the weight, and the body fat information of the user to the wireless module 205 so that the host computer 200 can manage the height, the weight, and the body fat information of the user to integrate the BMI value, BMR value, weight, body fat percentage, body water, muscle mass, analysis of muscle changes, body mineral content, arm circumference, and information on changes in waist, hip, or leg circumference of the user, and display the information for the user. The user can also wear the wireless sensor 110 to do the stepping exercise on the weight and body fat measurement part 90. Via the broadcast feature, the weight and body fat measurement part 90 can play music or a steady beat for the user to coordinate his or her movements with the sound played by the weight and body fat measurement part 90 to do the stepping exercise. The wireless sensor 110 can sense the heartbeat of the user and transfer the heartbeat information to the host computer 200; the weight and body fat measurement part 90 can also detect the exercise information on the stepping speed and rate of the user and transfer the exercise information on stepping to the host computer 200 so that the host computer 200 can manage the information and display the information for the user. However, the method of measuring the height and the weight are not limited to the abovementioned weight and body fat measurement part 90 and height measurement part 100; for example, the height measuring feature of the height measurement part 100 can be combined with the infrared light sensing feature of the muscular endurance test part 20, and the weight measuring feature of the weight and body fat measurement part 90 can be combined with the pressure sensing feature of the pressure sensing device of the muscular endurance test part 20; therefore, the muscular endurance test part 20 can combine the feature of weight measuring of the weight and body fat measurement part 90 and the feature of height measuring of the height measurement part 100.

As shown in FIG. 8 to FIG. 10, in the first embodiment of the present invention, the strength test part 70 is connected to the cardiopulmonary function test part 60, and the power storage part 160 is electrically connected to the cardiopulmonary function test part 60 and the strength test part 70. The strength test part 70 is used for testing the arm muscles of the user. When actually using the strength test part 70, the user can adjust the weight of the strength test part 70, sit on the muscular endurance test part 20, hold the strength test part 70, and pull the strength test part 70 such that the strength test part 70 can test the strength or the muscle endurance of the user. The strength test part 70 can transfer the muscle information of the user to the wireless module 205 so that the host computer 200 can manage the muscle information of the user and display the information for the user. The strength test part 70 can be set to test the strength for 1 to 3 times so that the host computer 200 can calculate the average strength or capture the best strength performance to serve as the final muscle information. The cardiopulmonary function test part 60 is used for testing the cardiopulmonary function of the user and is designed as bicycle pedals; when actually using the cardiopulmonary function test part 60, the user can sit on the muscular endurance test part 20 and use the pedals of the cardiopulmonary function test part 60 so that the cardiopulmonary function test part 60 can record the cardiopulmonary function information on stepping speed, calories burned, and distance traveled according to the stepping of the user, and transfer the cardiopulmonary function information of the user to the wireless module 205 so that the host computer 200 can manage the cardiopulmonary function information of the user and display the information for the user. The power storage part 160 is used for converting the kinetic energy generated by the exercising of the user into electricity and for storing the electricity; therefore, when the user uses the cardiopulmonary function test part 60 or the strength test part 70 to exercise, the power storage part 160 will convert the kinetic energy generated by the user when using the cardiopulmonary function test part 60 or the strength test part 70 into electricity and store the electricity for later provision to the multifunction fitness testing device 1 of the present invention or another electronic device to achieve the feature of energy saving.

Figure 11:
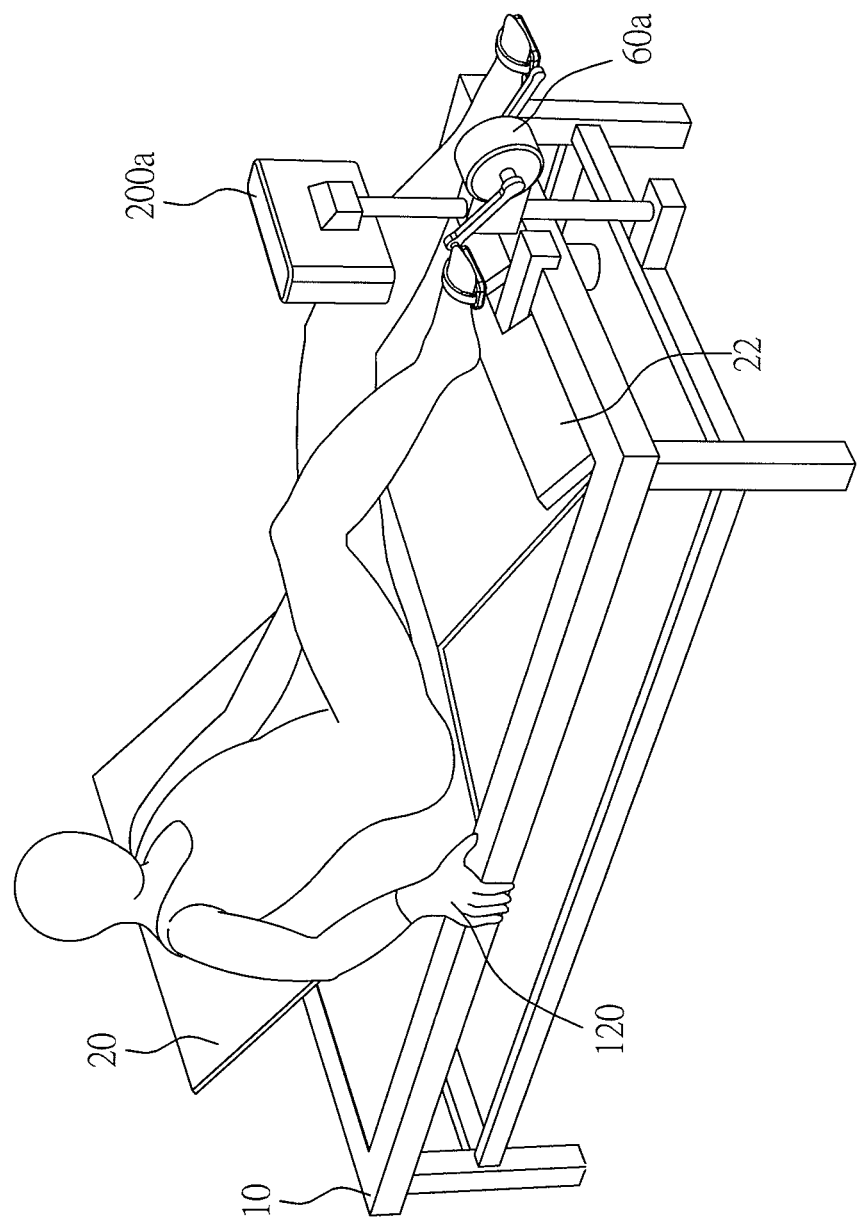
FIG. 11 illustrates a schematic drawing of the cardiopulmonary function test part of the multifunction fitness testing device of the second embodiment of the present invention.

Please refer to FIG. 11 regarding the multifunction fitness testing device of the second embodiment of the present invention. FIG. 11 illustrates a schematic drawing of the cardiopulmonary function test part of the multifunction fitness testing device of the second embodiment of the present invention.

The difference between the second embodiment and the first embodiment of the present invention is that, in the second embodiment, as shown in FIG. 11, the cardiopulmonary function test part 60a of the second embodiment is combined with the host computer 200a, and the cardiopulmonary function test part 60a and the host computer 200a are located next to the foot fixing part 22; therefore, the user can lie on the muscular endurance test part 20, step on the cardiopulmonary function test part 60a which is next to the foot fixing part 22 to do the cardiopulmonary exercise, and easily view the cardiopulmonary information shown by the host computer 200a, which is next to the foot fixing part 22.

Figure 12:
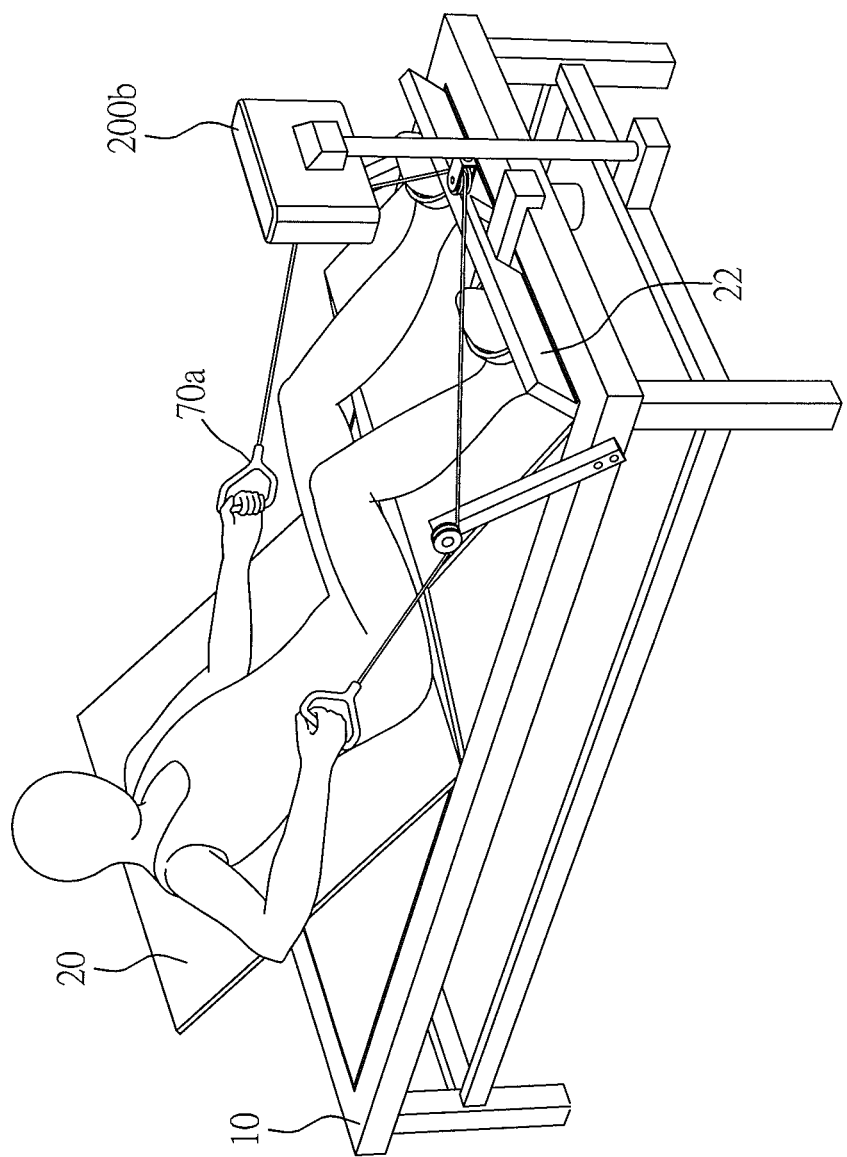
FIG. 12 illustrates a schematic drawing of the strength test part of the multifunction fitness testing device of the third embodiment of the present invention.

Please refer to FIG. 12 regarding the multifunction fitness testing device of the third embodiment of the present invention. FIG. 12 illustrates a schematic drawing of the strength test part of the multifunction fitness testing device of the third embodiment of the present invention.

The difference between the third embodiment and the first embodiment of the present invention is that, in the third embodiment, as shown in FIG. 12, the strength test part 70a of the third embodiment is combined with the host computer 200b, and the strength test part 70a and the host computer 200b are located next to the foot fixing part 22; therefore, the user can lie on the muscular endurance test part 20, use the strength test part 70a, which is next to the foot fixing part 22, to do the muscle test, and easily watch the muscle exercise information shown by the host computer 200a, which is next to the foot fixing part 22.

Figure 13:
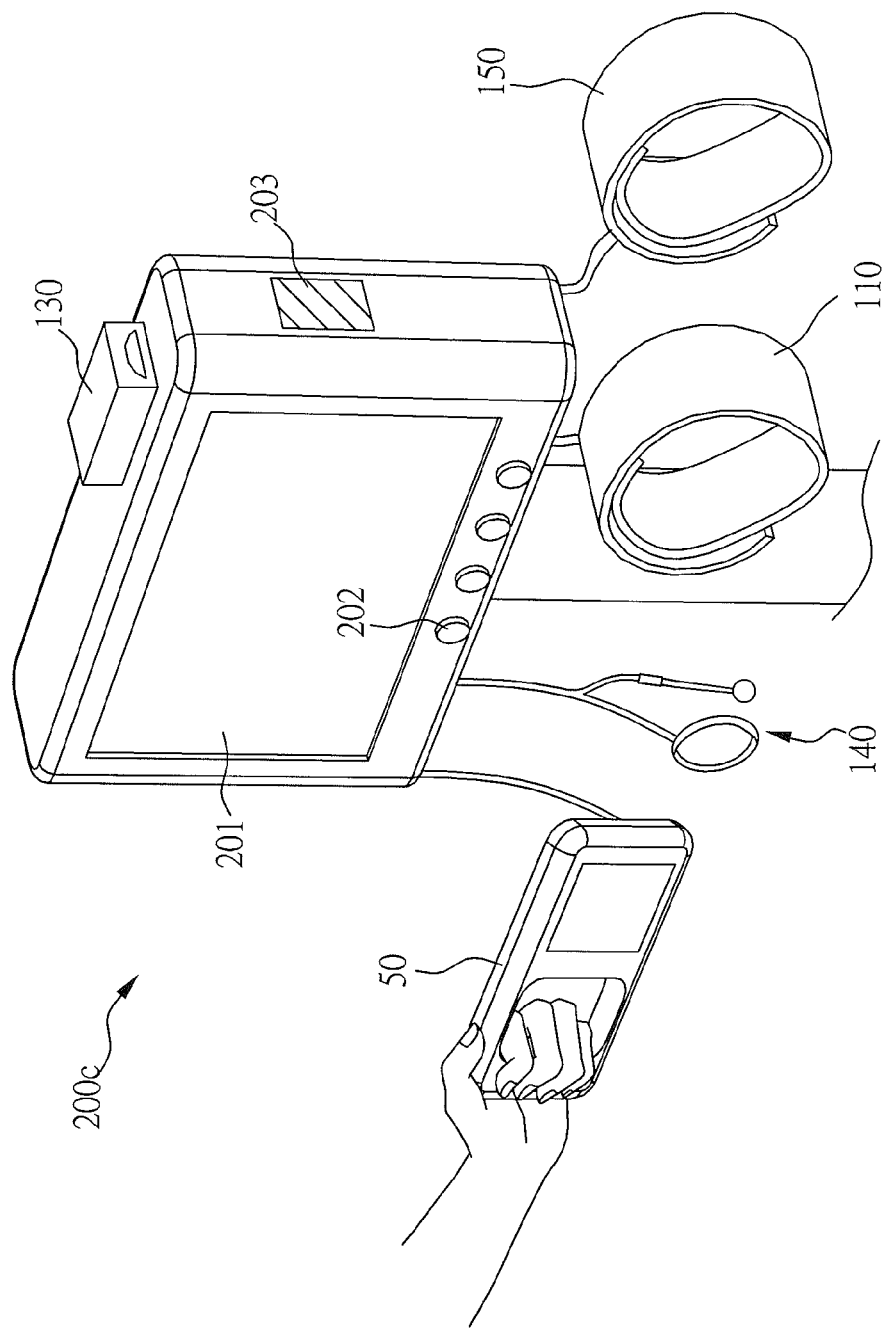
FIG. 13 illustrates a schematic drawing of the fingertip clamp, the wrist clamp, and the arm clamp of the multifunction fitness testing device of the fourth embodiment of the present invention.
Figure 14:
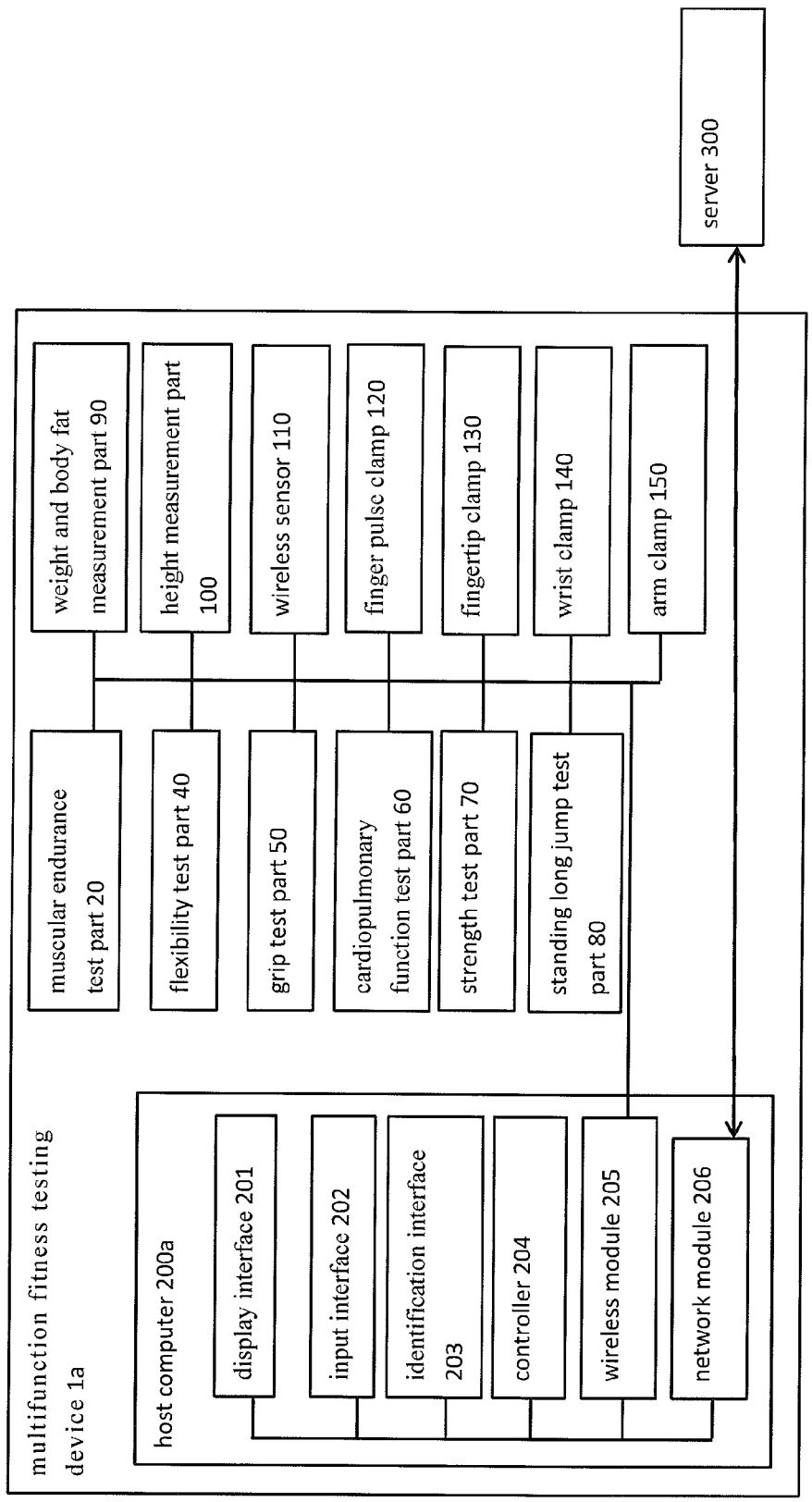
FIG. 14 illustrates a system schematic drawing of the multifunction fitness testing device of the fourth embodiment of the present invention.

Please refer to FIG. 13 and FIG. 14 about the multifunction fitness testing device of the fourth embodiment of the present invention. FIG. 13 illustrates a schematic drawing of the fingertip clamp, the wrist clamp, and the arm clamp of the multifunction fitness testing device of the fourth embodiment of the present invention. FIG. 14 illustrates a system schematic drawing of the multifunction fitness testing device of the fourth embodiment of the present invention.

The difference between the fourth embodiment and the first embodiment of the present invention is that, in the fourth embodiment, as shown in FIG. 13 and FIG. 14, the multifunction fitness testing device 1a further includes a fingertip clamp 130, a wrist clamp 140, and an arm clamp 150. The fingertip clamp 130, the wrist clamp 140, and the arm clamp 150 are electrically connected to the host computer 200 via the radio frequency method, but the method of electrically connecting is not limited to that design; the host computer 200 can also be electrically connected via a cable. The fingertip clamp 130 is used for fastening the fingertip of the user and for analyzing the blood of the user for the blood information, such as the blood glucose level and the blood oxygen saturation. The wrist clamp 140 has a wrist belt and a detection piece. The wrist belt is used for fastening the wrist clamp to the wrist of the user, and the detecting piece is used for sensing physiological phenomena such as the pulse, heartbeat, and nerve signals; when the user uses the wrist clamp 140, the wrist clamp 140 can detect the heartbeat, heart rate variability, and autonomic nervous system functioning of the user. The arm clamp 150 is used for covering the arm of the user and for detecting physiological phenomena, such as blood pressure and atrial fibrillation of the user. The fingertip clamp 130, the wrist clamp 140, and the arm clamp 150 can transfer the detected results to the host computer 200; the host computer 200 can manage the detected results and display the blood glucose concentration, oxygen saturation, electrocardiography, heart rate variability, autonomic nervous system functioning, blood pressure, or atrial fibrillation on the display interface 201.

It is noted that the above-mentioned embodiments are only for illustration. It is intended that the present invention cover modifications and variations of this invention provided they fall within the scope of the following claims and their equivalents. Therefore, it will be apparent to those skilled in the art that various modifications and variations can be made to the structure of the present invention without departing from the scope or spirit of the invention.

What is claimed is:

1. A multifunction fitness testing device, comprising:
   a main body;
   a muscular endurance test part connected to the main body, the muscular endurance test part comprising a folding plate and a foot fixing part,
   wherein the foot fixing part is connected to the folding plate;
   a flexibility test part located next to the foot fixing part;
   a grip test part; and
   a host computer connected to the main body and electrically connected to the folding plate, the flexibility test part, and the grip test part.

2. The multifunction fitness testing device as claimed in claim 1, further comprising a wireless sensor, wherein the wireless sensor is electrically connected to the host computer.

3. The multifunction fitness testing device as claimed in claim 2, further comprising a cardiopulmonary function test part, wherein the cardiopulmonary function test part is electrically connected to the host computer.

4. The multifunction fitness testing device as claimed in claim 3, further comprising a strength test part, wherein the strength test part is electrically connected to the host computer.

5. The multifunction fitness testing device as claimed in claim 4, further comprising a standing long jump test part, wherein the standing long jump test part is electrically connected to the host computer.

6. The multifunction fitness testing device as claimed in claim 5, further comprising a weight and body fat measurement part, wherein the weight and body fat measurement part is electrically connected to the host computer.

7. The multifunction fitness testing device as claimed in claim 6, further comprising a height measurement part, wherein the height measurement part is electrically connected to the host computer.

8. The multifunction fitness testing device as claimed in claim 7, further comprising a finger pulse clamp, wherein the finger pulse clamp is electrically connected to the host computer.

9. The multifunction fitness testing device as claimed in claim 8, further comprising a fingertip clamp, wherein the fingertip clamp is electrically connected to the host computer.

10. The multifunction fitness testing device as claimed in claim 9, further comprising a wrist clamp, wherein the wrist clamp is electrically connected to the host computer.

11. The multifunction fitness testing device as claimed in claim 10, further comprising an arm clamp, wherein the arm clamp is electrically connected to the host computer.

12. The multifunction fitness testing device as claimed in claim 11, wherein the host computer further comprises a display interface, an input interface, an identification interface, a controller, and a wireless module, and the controller is electrically connected to the display interface, the input interface, the identification interface, and the wireless module.

13. The multifunction fitness testing device as claimed in claim 12, wherein the host computer further comprises a network module electrically connected to the controller and a server.

14. The multifunction fitness testing device as claimed in claim 13, wherein the finger pulse clamp, the fingertip clamp, the wrist clamp, the arm clamp, the height measurement part, the wireless sensor, the cardiopulmonary function test part, the strength test part, the muscular endurance test part, the standing long jump test part, and the weight and body fat measurement part are electrically connected to the host computer via a radio frequency method.

* * * * *